United States Patent [19]

Pastrone

[11] Patent Number: 4,457,753
[45] Date of Patent: Jul. 3, 1984

[54] INTRAVENOUS METERING DEVICE
[75] Inventor: Giovanni Pastrone, Los Gatos, Calif.
[73] Assignee: Oximetrix, Inc., Mountain View, Calif.
[21] Appl. No.: 374,489
[22] Filed: May 3, 1982

Related U.S. Application Data

[63] Continuation-in-part of Ser. No. 278,954, Jun. 30, 1981, which is a continuation-in-part of Ser. No. 174,666, Aug. 1, 1980, Pat. No. 4,336,800.

[51] Int. Cl.³ .............................................. A61M 0/00
[52] U.S. Cl. .................................... 604/153; 417/435; 604/123; 128/DIG. 12
[58] Field of Search .......................... 417/38, 435, 443; 604/151–153, 118, 122–123, 246

[56] References Cited

U.S. PATENT DOCUMENTS 3,559,644  2/1971  Stoft et al. .......................... 604/123
3,620,650  11/1971  Shaw ................................... 417/417
4,140,118  2/1979  Jassawalla .......................... 604/123
4,142,524  3/1979  Jassawalla et al. ................. 604/123
4,236,880  12/1980  Archibald ...................... 604/123 X
4,336,800  6/1982  Pastrone ............................. 604/123

Primary Examiner—Dalton L. Truluck
Attorney, Agent, or Firm—Robert S. Kelly

[57] ABSTRACT

An improved intravenous metering device (1a) having a measuring chamber (77) for use in measuring the discharge pressure of fluid exiting the device (1) is disclosed. The discharge pressure measuring chamber (77), which operates in conjunction with a pin (63) and flexure beam (65) arrangement to provide an indication of fluid discharge pressure, is incorporated into the fluid flow path through the device in order to permit sweeping of gas bubbles from the chamber (77) during device priming operations. Thus, complete removal of gas bubbles from the device (1a) prior to employing the device with a patient is more easily attainable.

7 Claims, 7 Drawing Figures

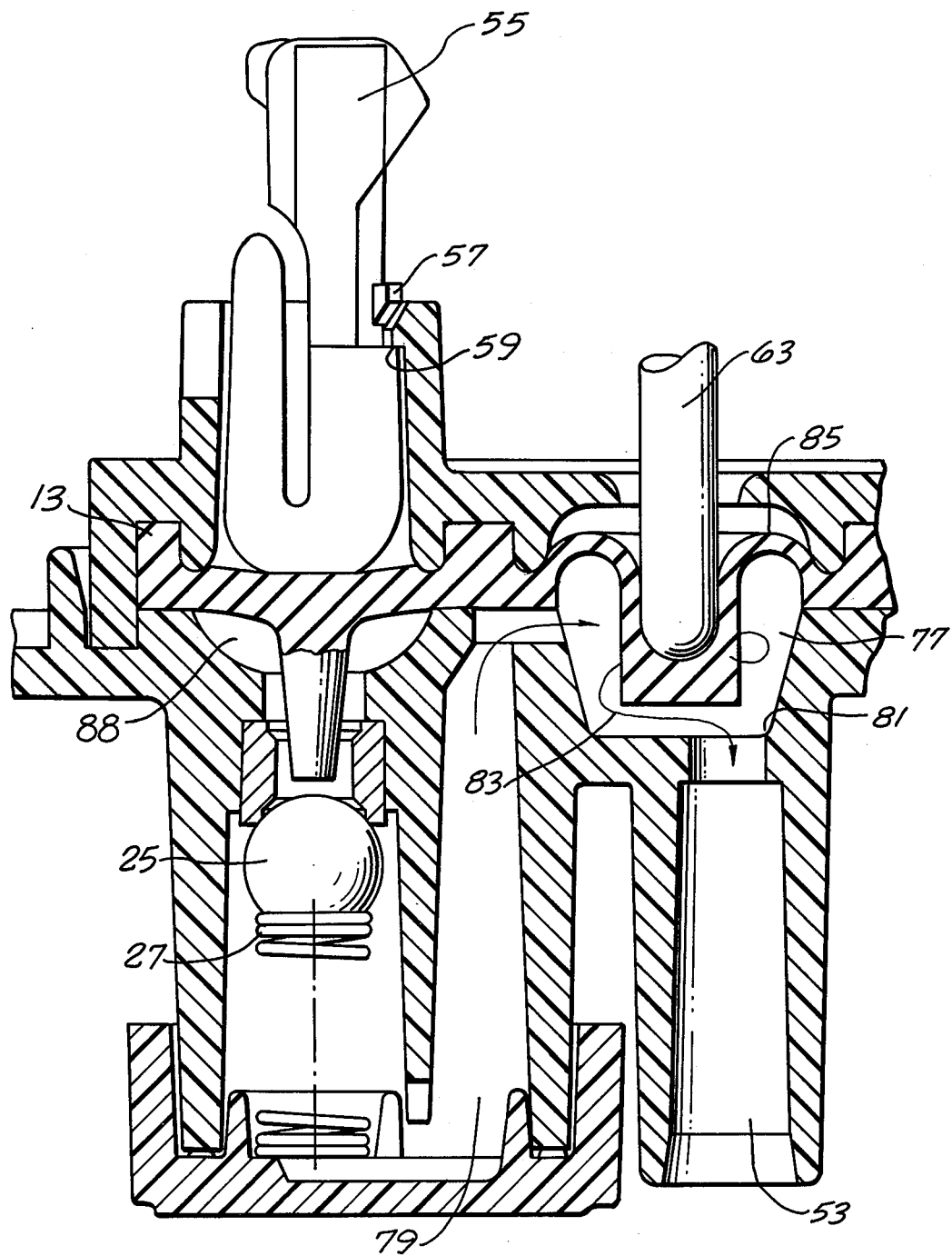
FIG_7_

INTRAVENOUS METERING DEVICE

RELATED APPLICATIONS

This application is a continuation-in-part of co-pending U.S. application Ser. No. 278,954 filed June 30, 1981 and titled Intravenous Metering Device, which is in turn a continuation-in-part of co-pending U.S. application Ser. No. 174,666 filed Aug. 1, 1980 and titled Intravenous Metering Device, now U.S. Pat. No. 4,336,800 issued June 29, 1982.

TECHNICAL FIELD

The present invention relates to intravenous metering devices in general and is more particularly directed to an intravenous metering device wherein fluid discharge pressure from the device can be accurately measured without introducing gas bubbles into the fluid flowing through the device.

BACKGROUND ART

Considerable attention in recent years has been directed to the intravenous delivery of fluids such as saline solutions and the like to patients. Initially, these fluids were administered to the patient by means of gravity flow from a container holding the fluid to be delivered. Gravity-flow devices, however, proved cumbersome to use, inasmuch as pressure sufficient to sustain fluid movement in a gravity-flow device often required positioning of the device at a considerable elevation above the patient receiving the fluid. Moreover, attempts to accurately regulate the amount of fluid administered by gravity-flow devices were often unsuccessful because of the fact that the gravity-induced pressure responsible for moving fluid through the device generally decreased as the fluid level within the container holding the fluid dropped during the intravenous delivery operation.

SUMMARY OF THE INVENTION

The improved intravenous metering device of the present invention utilizes a pumping chamber from which liquid is periodically pumped to the patient through an outlet at the lower end thereof. As an integral part of the device there is provided a measuring chamber which serves to measure the discharge pressure of the liquid that is pumped from the pumping chamber in order to detect potentially dangerous downstream conditions requiring pump slowdown or pump shutoff. A passageway extends upwardly from the pumping chamber outlet to the upper end of the measuring chamber, and the outlet from the measuring chamber is at the lower end thereof. Thus, when the device is initially primed with liquid prior to connection to a patient by inverting the device and opening the outlet valve at the outlet of the pumping chamber, liquid fills both the pumping chamber and the discharge chamber from the bottom up so as to sweep all air from the chambers and preclude the trapping of any air therein.

The various features, objects and advantages of the present invention will become apparent upon consideration of the following Brief Description of the Drawings, Best Mode for Carrying Out the Invention, and the Claims.

BRIEF DESCRIPTION OF THE DRAWINGS

FIG. 7 is a partial cross-sectional view taken along line VII—VII of FIG. 6.

BEST MODE FOR CARRYING OUT THE INVENTION

Figure 1:
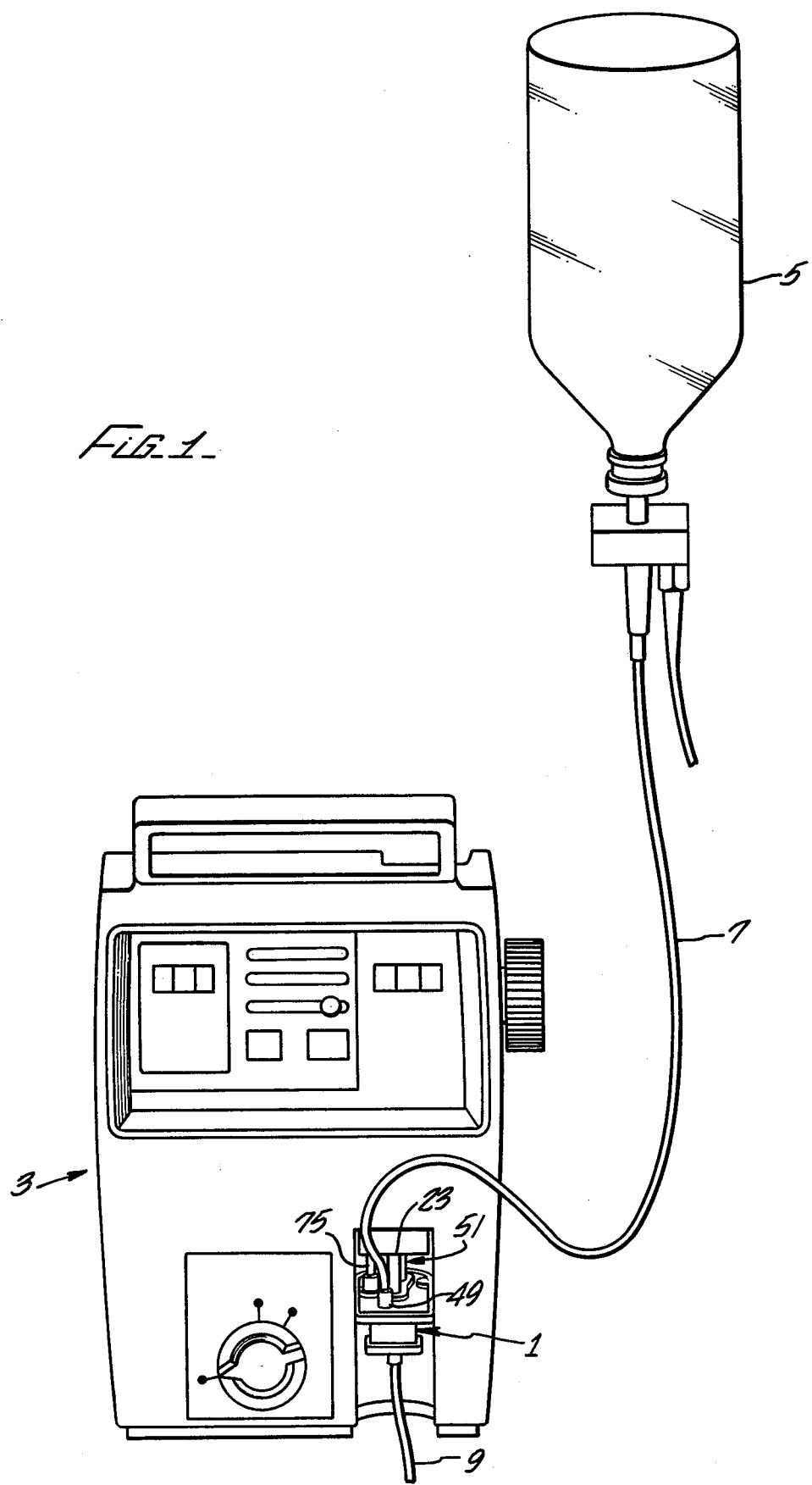
FIG. 1 is a pictorial view illustrating the use of the intravenous metering device of the present invention.

Referring first to FIG. 1, an intravenous metering device 1 is shown positioned within a metering device control unit 3. The intravenous metering device 1 is connected to a container of fluid 5 by means of conventional tubing 7. Tubing 9, extending from the outlet of the intravenous metering device 1, transfers precise amounts of fluid to the patient being treated.

Figure 2:
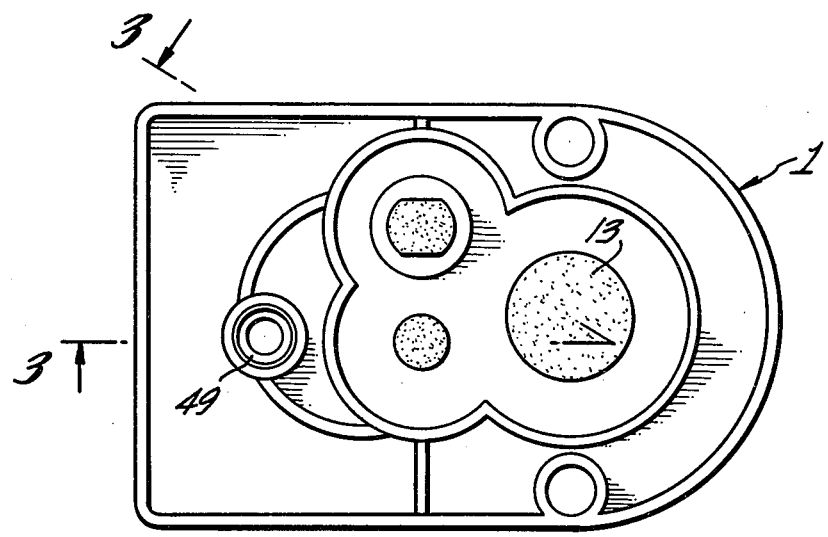
FIG. 2 is a top view showing an intravenous metering device of a type useful with the present invention.
Figure 3:
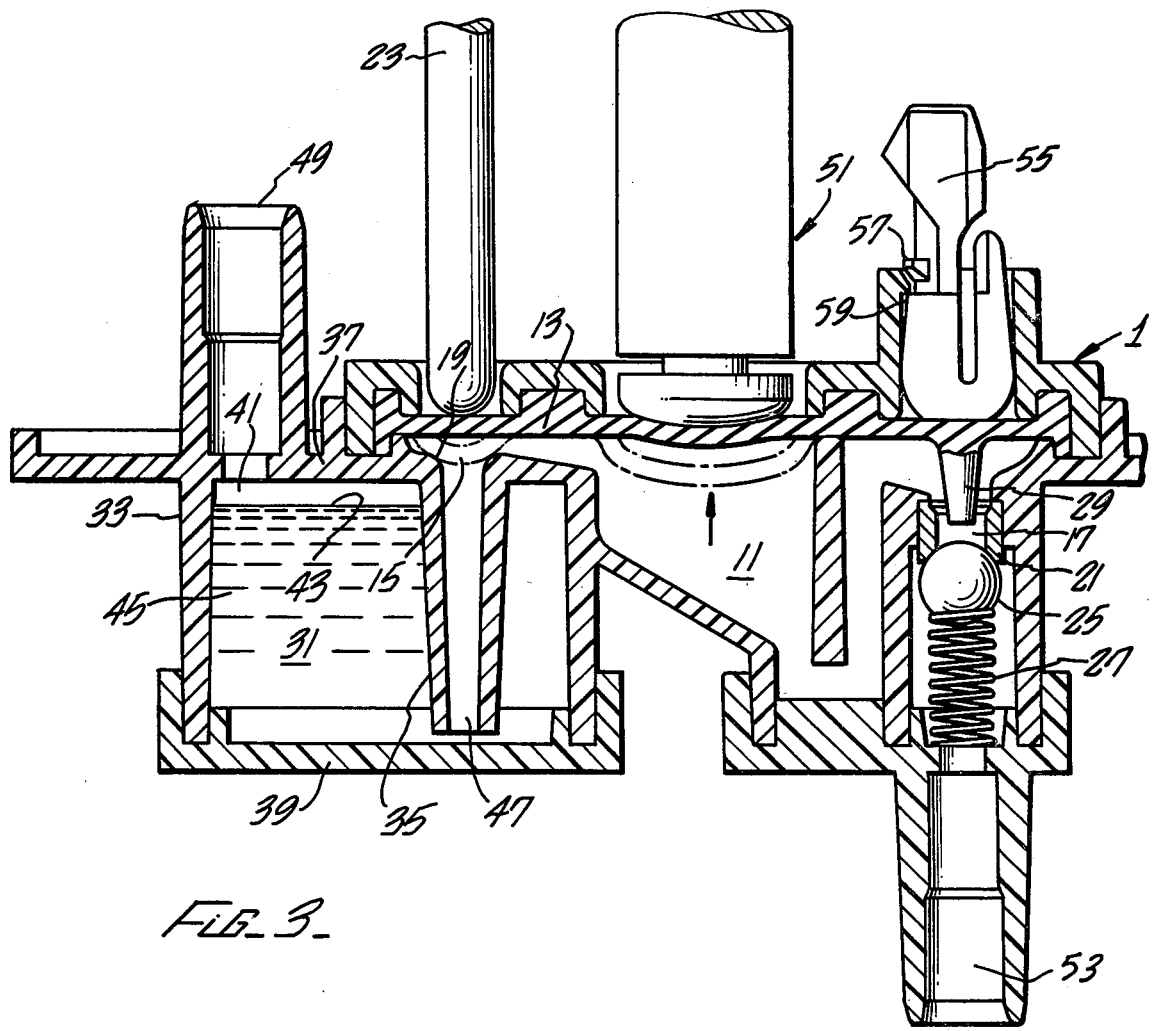
FIG. 3 is a partial cross-sectional view illustrating the intravenous metering device of FIG. 2.

Turning next to FIGS. 2 and 3, the construction of intravenous metering device 1 is shown in detail. The intravenous metering device 1 includes a pumping chamber 11 and a flexible diaphragm 13 which forms a portion of the pumping chamber 11. A pumping chamber inlet 15 and a pumping chamber outlet 17 are formed in pumping chamber 11. Pumping chamber 15 includes a valve seat means 19. Similarly, pumping chamber outlet 17 includes a valve seat means 21. Valve actuator 23 controls the admission of fluid into pumping chamber 11 by reciprocating the diaphragm 13 between an open position, shown in solid lines in FIG. 3, and a closed position as shown by dotted lines in FIG. 3. A ball check 25 is positioned such that it seats against valve seat 21 of pumping chamber outlet 17. The ball check 25 is normally held in a closed position by biasing means such as spring 27. The flexible diaphragm 13 has a projection 29 opposite ball check 25.

Intravenous metering device 1 further includes a gas retention chamber 31 bounded by sidewalls 33 and opposed walls 37 and 39. As shown in FIG. 3, the gas retention chamber 31 is of sufficient size to include a gas retention chamber upper portion 41 providing for a gas-liquid interface 43. Gas retention chamber 31 also includes a gas retention chamber lower portion 45 from whence fluid free of gas bubbles may pass through a gas retention chamber passageway 47 in tubular conduit 35 and on into the pumping chamber 11.

Pumping operation of intravenous metering device 1 is initiated by reciprocating a pumping piston 51 against flexible diaphragm 13, whereupon fluid free of gas bubbles is pumped through the intravenous metering device as described below. The position of diaphram 13 shown by solid lines in FIG. 3 illustrates the condition of the diaphragm when the pumping piston 51 is in the upstroke position while the dotted line position of diaphragm 13 in FIG. 3 illustrates the position of the diaphragm in the associated down-stroke position of pumping piston 51.

The detailed construction of intravenous metering device 1 having been set forth, the method of operating the intravenous metering device will now be discussed. When intravenous metering device 1 is to be filled, or primed, the device is rotated 180° i.e., it is inverted, and manual latch valve 55 is depressed such that stop 57 engages shoulder 59 of the body of intravenous metering device 1. Flexible diaphragm projection 29 is thus forced into contact with ball check 25 and spring 27 is compressed so as to allow the passage of fluid from metering device inlet 49 through the gas retention chamber 31 and the pumping chamber 11 to the outlet tubing 9. Because (with the device inverted) each of the chambers 31 and 11 ae filled by directing the liquid into the bottom thereof and allowing it to uniformly fill the chambers upwardly, the relatively constant, high velocities of fluid flow are experienced during the filling operation of the intravenous metering device 1. Such relatively constant high velocities assist in sweeping gases from pumping chamber 11 prior to use of the intravenous metering device, consequently enabling the intravenous metering device 1 to administer fluid free of gas bubbles to a patient.

Following the filling operation, intravenous metering device 1 is returned to its upright position and inserted into metering device control unit 3. Incoming fluid, transmitted by tubing 7 to the intravenous metering device inlet 49, subsequently passes into the gas retention chamber 31 which, due to the downward extension of outlet tube 35, prevents any gases therein from entering the pumping chamber 11 and allows for the generation of a gas-liquid interface 43 in the gas retention chamber upper portion 41. Fluid free of gas bubbles passes from the gas retention chamber lower portion 45 through passageway 47. When valve actuator 23 is reciprocated upwardly, fluid free of gas bubbles is allowed to pass into pumping chamber 11. Valve actuator 23 is then closed. As the flexible diaphragm 13 is moved downwardly by means of the pumping piston 51, the volume within the pumping chamber 11 is decreased and the pressure within the pumping chamber 11 overcomes the biasing means 27 urging pumping chamber outlet ball check 25 against pumping chamber outlet valve seat 21, thereby allowing a precise amount of metered fluid to be pumped from pumping chamber 11 through the intravenous metering device outlet 53 to a patient. The intravenous metering device 1 of the present invention may be disposable, permitting a fresh and sterilized intravenous metering device 1 to be employed for each delivery of intravenous fluid to a patient.

Figure 4:
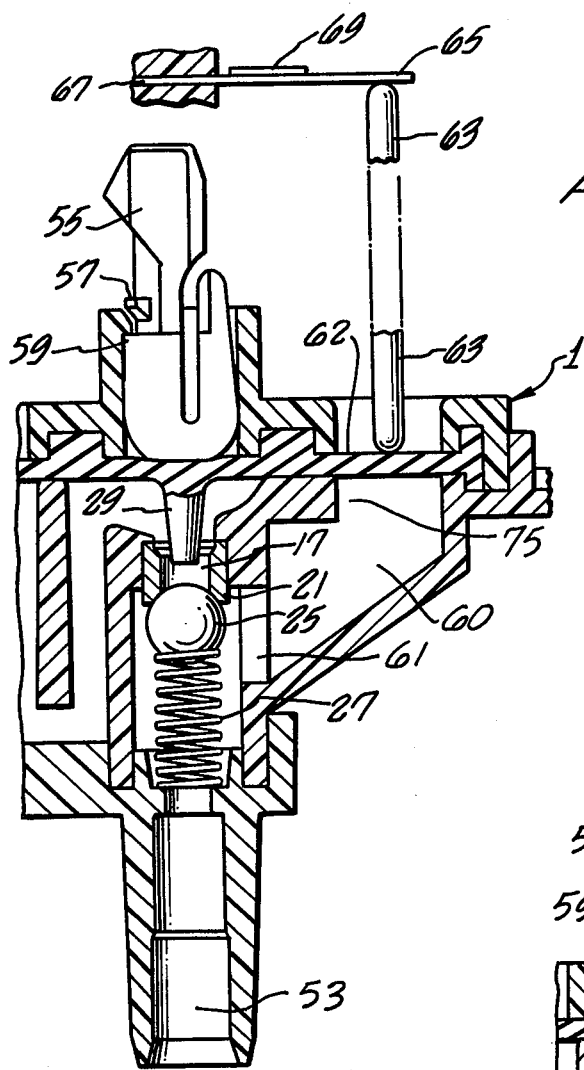
FIGS. 4 and 5 are partial cross-sectional views illustrating the prior means for measuring discharge pressure from the intravenous metering device of FIG. 2.
Figure 5:
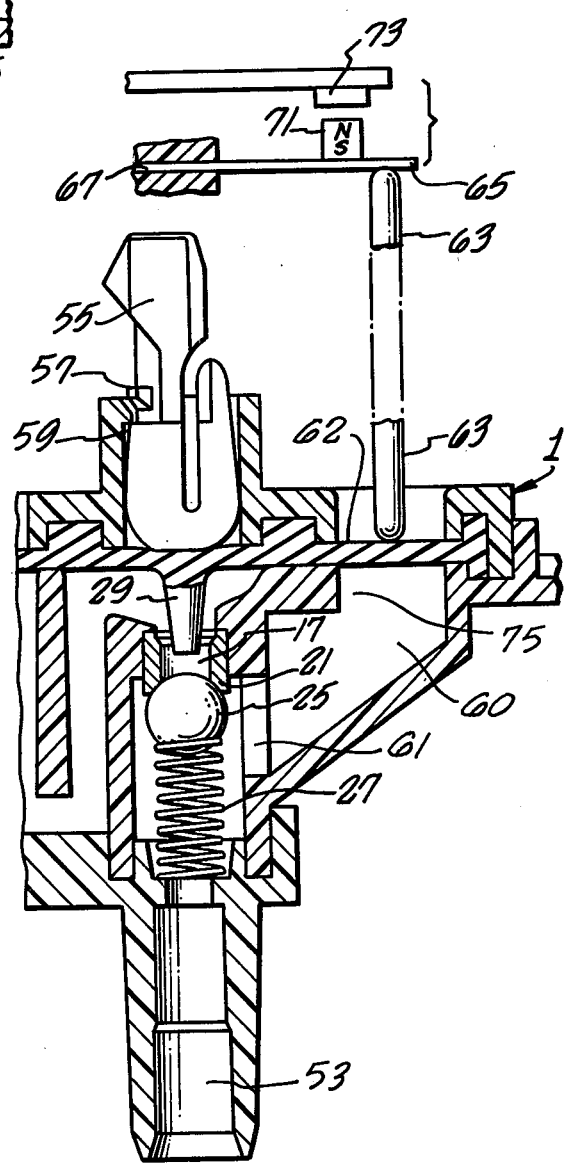

It is important to measure the discharge pressure of liquid leaving intravenous metering device 1. Excessive discharge pressure may indicate a plugged filter or discharge line occlusion requiring correction. Accordingly, in accordance with the present invention, the intravenous metering device 1 has been modified to include a pressure indicating means for determining discharge pressure. FIGS. 4 and 5 illustrate prior attempts to provide such a pressure indicating means. Referring first to FIG. 4, a discharge pressure measuring chamber 60 is positioned downstream of ball check 25 and communicates with intravenous metering device outlet 53 via port 61. A portion 62 of flexible diaphragm 13 defines the upper wall of discharge pressure measuring chamber 60. A discharge pressure pin 63 is mounted in a retainer structure (not shown) above diaphragm portion 62. The discharge pressure pin 63 slides freely in the retainer structure and is oriented such that diaphragm portion 62 is forced upward against the discharge pressure pin as the discharge pressure of fluid passing through pumping chamber outlet 17 and intravenous metering device outlet 53 increases. The resultant movement of discharge pressure pin 63 produces movement of a flexure beam 65, one end 67 of which is anchored to a fixed support. The movement of flexure beam 65 in turn is translated into a pressure read-out through employment of a conventional strain gauge 69. Alternately, as shown in FIG. 5, the movement of flexure beam 65 may be translated into a pressure read-out by using the combination of a magnet 71 attached to the flexure beam and a Hall Effect Device 73 for measuring the change in electron flow as the magnetic field about the Hall Effect Device 73 is altered by movement of magnet 71. A more detailed explanation of Hall Effect Devices may be found in "Hall Effect Devices and Their Applications," *Electronics Industry*, May 1979, pp. 17–21.

Figure 6:
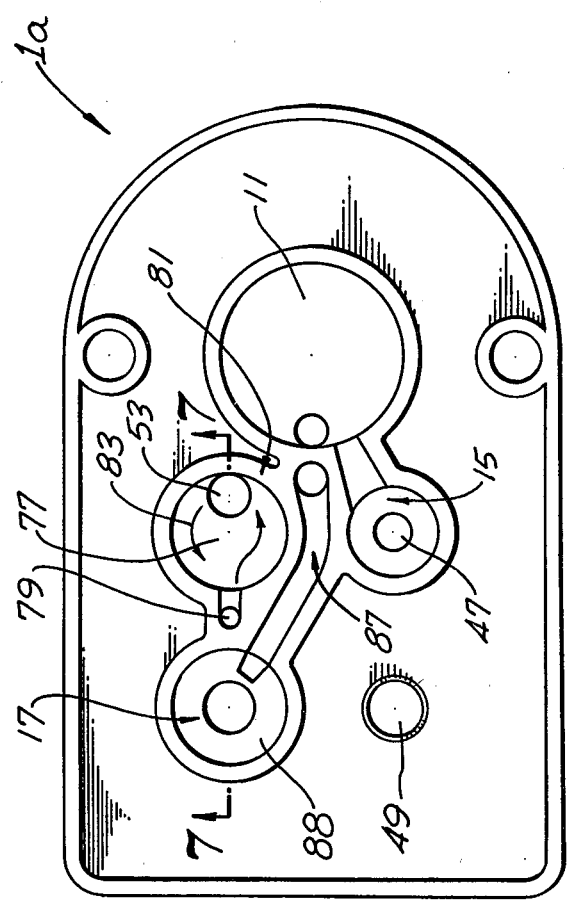
FIG. 6 is a top view of the FIG. 2 intravenous metering device with the flexible diaphragm thereof removed and modified to include the discharge pressure measuring chamber of the present invention.

As previously indicated, the positioning of the inlet to the pumping chamber 11 is designed to create a liquid flow path which fosters high fluid flow velocities through pumping chamber 11 for the purpose of sweeping out gas bubbles present in the pumping chamber during the intravenous metering device filling operation. In the discharge pressure measuring devices of FIGS. 4 and 5, however, it will be seen that the discharge pressure measuring chamber 60 contains many abrupt angles and surfaces which create pockets and has a dead-end pocket 75 capable of trapping air or other gas bubbles during filling which will remain when the fluid metering device 1 is turned back around to an upright position in preparation for pumping operations. Air or gas bubbles so trapped may subsequently escape into the fluid flow, leaving the intravenous metering device outlet 53 and entering into the delivery tubing 9 despite the precautions taken in performing the intravenous metering device filling operation. In order to avoid this undesirable consequence and in accordance with the present invention, the discharge pressure measuring chamber itself is incorporated into the fluid flow path leaving pumping chamber outlet 17 so that the filling thereof will be accomplished in generally the same manner as with the pumping chamber 11. Thus, as shown in FIGS. 6 and 7, intravenous metering device 1a is constructed with a discharge pressure measuring chamber 77 and a relocated intravenous metering device outlet 53 positioned at the base of the discharge pressure measuring chamber 77. An intermediate passageway 79 is formed to carry fluid from the pumping chamber outlet 17 past ball check 25 and spring 27 into the discharge pressure measuring chamber 77 entering at the upper end thereof (the lower end when the device is inverted for priming). The outlet 81 of the chamber 77 is at the bottom thereof (at the top during initial filling) so that, the discharge pressure measuring chamber is made a part of the fluid flow path through intravenous metering device 1. The sweeping action of the fluid established during the intravenous metering device filling operation previously described will thus continue on into the discharge pressure measuring chamber 77 when the intravenous metering device is inverted for filling purposes, removing gas otherwise present in the intravenous metering device 1 from the discharge pressure measuring chamber 77 as well as the pumping chamber 11. The intravenous metering device outlet 53 is offset to one side of discharge pressure measuring chamber 77, as indicated by outlet 81 and the diaphragm portion 85 of diaphragm 13 that surrounds the pin 63 extends centrally within the chamber, thereby creating a swirling fluid flow path 83 through the discharge pressure measuring chamber 77 as fluid exits the intravenous metering device 1 via intravenous metering device outlet 53. This swirling fluid flow path aids in sweeping gas out of the discharge pressure measuring chamber 77 when the intravenous metering device is filled.

Discharge pressure pin 63 is again oriented over portion 85 of diaphragm 13 which covers the discharge pressure measuring chamber 77 as shown, and movement of the discharge pressure pin 73 in response to upward motion of diaphragm portion 85 can be translated into a discharge pressure reading by employing either of the measuring schemes illustrated in FIGS. 4 and 5. As also indicated in FIGS. 6 and 7, the shifting of the intravenous metering device elements in order to incorporate the discharge pressure measuring chamber 77 in the fluid flow path through the intravenous metering device requires the placement of the pumping chamber outlet 17, valve seat means 21 and ball check 25 at a location somewhat remote from pumping chamber 11. Thus, a separate pumping chamber portion 88 is provided at a position removed from the main portion of pumping chamber 11, and an elongated passageway 87 must therefore be formed in the intravenous metering device 1 to transport fluid from the pumping chamber 11 to the pumping chamber outlet 17 which is provided at the bottom of pumping chamber portion 88.

The present invention has been set forth in the form of one preferred embodiment. It is nevertheless intended that modifications to the intravenous metering device disclosed herein may be made by those skilled in the art without departing from the scope and spirit of the present invention. Moreover, such modifications are considered to be within the purview of the appended claims.

I claim:

1. A device which precisely meters liquids for intravenous delivery from a liquid source to a patient, said device comprising:
    a support structure including a device inlet for receiving liquid from the liquid source and a device outlet for removing liquid from said device;
    a pumping chamber permitting liquid to be pumped from the liquid source to the patient, said pumping chamber having an inlet at the upper end of the chamber in communication with said device inlet and an outlet at the lower end of at least a portion of the chamber in communication with said device outlet;
    an inlet valve at said pumping chamber inlet for blocking the flow of liquid out of said pumping chamber during pumping and for permitting the flow of liquid into said chamber between pumping periods;
    an outlet valve at said pumping chamber outlet, said outlet valve being biased closed and being opened under the pressure created in the pumping chamber during a pumping period;
    means defining a passage extending upwardly from the outlet of said pumping chamber;
    a discharge pressure measuring chamber communicating at its upper end with the upper end of said passage and communicating at its lower end with the device outlet;
    a flexible diaphragm member forming a portion of the wall of the discharge pressure measuring chamber for measuring the discharge pressure of fluid pumped by said pumping means; and
    a means for disabling said outlet valve to open the outlet of the pumping chamber whereby, by inverting the device, the device can be filled with liquid from the inlet to the outlet thereof without trapping air therein.

2. A device according to claim 1 wherein said flexible diaphragm member extends over both said pumping chamber and said pressure measuring chamber and provides the means for pumping liquid from said pumping chamber.

3. A device according to claim 1 wherein said flexible diaphragm member extends downwardly into said pressure measuring chamber so as to provide a swirling liquid flow path through the pressure measuring chamber during the initial filling thereof.

4. A device which precisely meters liquids for intravenous delivery from a liquid source to a patient, said device comprising:
    a support structure including a device inlet for receiving liquid from the liquid source and a device outlet for removing liquid from said device;
    a pumping chamber permitting liquid to be pumped from the liquid source to the patient, said pumping chamber having an inlet in communication with said device inlet and an outlet at the lower end of at least a portion of the pumping chamber, said outlet being in fluid communication with said device outlet;
    a passageway extending upwardly from the pumping chamber outlet; and
    a measuring chamber connected between said passageway and said device outlet, said measuring chamber including a reciprocable, pressure-sensitive member for measuring the discharge pressure of liquid pumped from said pumping chamber, said measuring chamber having an inlet at the upper end thereof in communication with the upper end of said passageway and an outlet at the lower end thereof in communication with the device outlet whereby flow through said measuring chamber during initial filling of said device with liquid precludes the trapping of air therein.

5. A device according to claim 4 wherein said pressure sensitive member comprises a flexible diaphragm.

6. A device according to claim 5 wherein said diaphragm extends over both said pumping chamber and said measuring chamber and provides the means for pumping liquid from said pumping chamber.

7. A device according to claim 6 wherein said diaphragm extends downwardly into said pressure measuring chamber so as to provide a swirling liquid flow path through the pressure measuring chamber during the initial filling thereof.

* * * * *